United States Patent
Cavazzuti et al.

(10) Patent No.: US 6,444,212 B1
(45) Date of Patent: Sep. 3, 2002

(54) MOISTURIZING AND LONG-WEARING MAKE-UP COMPOSITION

(75) Inventors: Roberto Cavazzuti, Westfield; Brian K. Mattox, Plainfield; Michael Swanborough, Avenel, all of NJ (US)

(73) Assignee: L'Oreal, Clichy (FR)

( * ) Notice: Subject to any disclaimer, the term of this patent is extended or adjusted under 35 U.S.C. 154(b) by 0 days.

(21) Appl. No.: 09/276,931

(22) Filed: Mar. 26, 1999

Related U.S. Application Data

(60) Provisional application No. 60/079,380, filed on Mar. 26, 1998, and provisional application No. 60/079,846, filed on Mar. 27, 1998.

(51) Int. Cl.$^7$ ............................ A61K 6/00; A61K 7/00; A61K 7/021; A61K 7/025
(52) U.S. Cl. ........................................ 424/401; 424/64
(58) Field of Search ............................ 424/401, 63, 64

(56) References Cited

U.S. PATENT DOCUMENTS

| | | | | |
|---|---|---|---|---|
| 5,505,937 A | * | 4/1996 | Castrogiovanni et al. | 424/64 |
| 6,080,390 A | * | 6/2000 | Calello et al. | 424/64 |
| 6,086,859 A | * | 7/2000 | Calello et al. | 424/64 |

FOREIGN PATENT DOCUMENTS

| WO | WO99/09937 | 3/1999 |
|---|---|---|

\* cited by examiner

*Primary Examiner*—Thurman K. Page
*Assistant Examiner*—S. Howard
(74) *Attorney, Agent, or Firm*—Oblon, Spivak, McClelland, Maier & Neustadt, P.C.

(57) ABSTRACT

A cosmetic composition which can be used for caring for and/or for making up the human face, in particular, the skin, eyelids, or lips, comprising at least one wax, at least one ester, and at least one long chain alcohol.

42 Claims, No Drawings

MOISTURIZING AND LONG-WEARING MAKE-UP COMPOSITION

RELATED APPLICATIONS

This application claims priority to U.S. provisional application Ser. Nos. 60/079,380 and 60/079,846, filed Mar. 26, 1998, and Mar. 27, 1998, respectively. Applicants have filed a related application (attorney docket no. 6388-384-55X) on the same date as the present application. The content of these applications is incorporated herein by reference.

FIELD OF THE INVENTION

The present invention relates to a cosmetic composition which can be used for caring for and/or for making up the human face, in particular, the skin, eyelids, or lips.

BACKGROUND OF THE INVENTION

Cosmetic compositions such as lipsticks and foundations generally comprise fatty substances, such as oils, pasty compounds and waxes, as well as a particulate phase generally composed of fillers and of pigments. These compositions can also contain cosmetic or dermatological active principles (vitamins, screening agents, moisturizers). However, when applied on the skin, eyelids, or lips, these compositions exhibit the disadvantage of transferring. In other words, the composition is deposited, at least in part, on certain substrates with which it is brought into contact, such as, for example, a glass or cup, an item of clothing, or the skin. On being deposited, the composition leaves a mark on the substrate. The result is thus a mediocre persistence of the composition on the skin, eyelids, or lips, requiring it to be reapplied regularly. Moreover, the appearance of unacceptable marks on certain items of clothing and in particular on the collars of shirts or blouses might dissuade some consumers from using this type of makeup.

Another disadvantage of these compositions lies in the problem of migration. It has been found that certain cosmetic compositions have a tendency to spread into the fine lines and/or wrinkles of the skin, in the case of foundations; into the fine lines which surround the lips, in the case of lipsticks; and into the folds of the eyelid, in the case of eyeshadows. Streaks in the makeup may also occur, particularly in the case of eyeshadows due to the movements of the eyelids.

All these phenomena produce an unsightly effect which it is very clearly desirable to avoid.

For a number of years, cosmetic scientists have been interested in long-wearing cosmetic compositions, in particular lipstick or foundation compositions. Some of these compositions contained silicone derivatives which, when combined with other ingredients, resulted in a lipstick which, although longer-wearing than previous lipsticks, left an uncomfortable dry, tight feeling on the lips. Additionally the long-wearing cosmetic compositions generally had a matte finish rather than the more desirable shiny finish. The art has continued to search for a composition combining moisturizing and long-wearing attributes.

SUMMARY OF THE INVENTION

Now, the inventors have discovered, unexpectedly and surprisingly, a long-wearing cosmetic composition which provides a film which substantially does not transfer or migrate and which additionally exhibits improved properties with respect to those of the long-wearing products of the prior art, in particular moisturizing, softening, and shine.

In order to achieve these and other advantages, the present invention is drawn to a cosmetic compositions comprising at least one wax, at least one ester, and at least one long chain alcohol. The composition may further comprise at least one film-forming agent and at least one volatile silicone derivative. In addition, the composition of the invention contains substantially no fluorinated oils.

DETAILED DESCRIPTION OF THE PREFERRED EMBODIMENTS

Waxes

The waxes that may be used in the present invention include, but are not limited to, waxes of animal, vegetable, mineral and synthetic origin, such as ozokerite, candelilla, and carnauba waxes, polyethylene waxes, microcrystalline waxes, silicone waxes, paraffin, petrolatum, montan wax, beeswax, Japan wax, ouricury wax, lanolin and its derivatives, cocoa butter, sugarcane or cork fiber waxes, hydrogenated oils which are solid at 25° C., waxes obtained by the Fisher-Tropsch synthesis, and mixtures thereof. Preferably, the waxes used in the present invention have a melting point greater than 45° C. and are selected from ozokerite, available as, for example, OZOKERITE 170 from Strahl and Pitsch, microcrystalline wax, available as, for example, MULTIWAX W-445 from Witco, and polyethylene, available as, for example, PERFORMALENE 400 from New Phase Technologies. The at least one wax of the invention is preferably present in an amount of from about 1% to about 35%, including about 1% to about 30%, about 1% to about 25%, or about 3% to about 20%.

An ethylene homopolymer or ethylene copolymer having a melting point of 30 to 135° C. may be used. Such ethylene homopolymer or ethylene copolymer will have a molecular weight ranging from about 100 to about 2,000. Preferably the ethylene copolymers are comprised of ethylene monomer units of the following formula:

$$CH_2=CH-R_1$$

wherein $R_1$ is a $C_{1-30}$ straight or branched chain saturated or unsaturated alkyl, aryl, or aralkyl, preferably a $C_{1-10}$ straight or branched chain alkyl. Examples of ethylene homo- and copolymers which may be used in the invention are set forth in U.S. Pat. No. 5,556,613, which is hereby incorporated by reference.

Esters

The esters that are useful in the presently claimed composition are esters obtained from acids having at least 4 carbon atoms such as, but not limited to, citric acid, octanoic acid, palmitic acid, hydroxystearic acid, stearic acid, oleic acid, arachidonic acid, myristic acid, and isostearic acid. These esters include $C_{12-22}$ fatty esters of citric acid. Preferred esters include, but are not limited to, citrate esters, dipentaerythrityl esters, and dilinoleate esters. Particularly preferred esters are dipentaerythrityl tetrahydroxystearate/isostearate, triisostearyl citrate and mixtures thereof. Dipentaerythrityl tetrahydroxystearate/isostearate is available, for example, from Nisshin Oil Mill under the trade name COSMOL 168E. The at least one ester of the invention is preferably present in an amount ranging from about 5% to about 40%. Where two esters are used, the combined amount may range from about 10% to about 60%. In a preferred embodiment, triisostearyl citrate is used in an amount of 5% to about 19% by weight, and optionally dipentaerythrityl tetrahydroxystearate/isostearate in an amount of 10% to about 20% by weight.

Long Chain Alcohols

The long chain alcohols useful in the presently claimed invention preferably have at least 8 carbon atoms in a linear or branched chain. Preferably, the long chain alcohols useful in the claimed invention contain from 12 to 48 carbon atoms. Such long-chain alcohols include, but are limited to, octyldodecanol, octyltetradecanol, octahexadecanol, oleyl alcohol, linoleyl alcohol, linolenyl alcohol, cetyl alcohol, lauric alcohol, lauryl glycol, hexadecylic alcohol, and isostearyl alcohol. Octyldodecanol, available from Henkel as EUTANOL G, is particularly preferred. The at least one long chain alcohol of the invention is preferably present in an amount ranging from 1 to 40%. The straight or branched chain fatty alcohols may also be used in amounts of from about 1% to about 35%.

Film-forming Agents

Film-forming agents which can be used in the inventive composition may be selected from any film-forming agents commonly known in the art. Among the film-forming polymers which may be used, mention may be made of synthetic polymers, polymers of natural origin and mixtures thereof. Preferably, the film-forming agent is a polyvinyl pyrrolidone (PVP) copolymer such as GANEX V216 (PVP/hexadecene), GANEX V220 (PVP/eicosene), or GANEX WP 660 (PVP/tricontanyl), available from ISP, or a polypropylene glycol/sodium maleic acid diisobutylene copolymer such as POLYOLPREPOLYMER-2 (PPG-12/SMDI) and POLYOLPREPOLYMER-14 (PPG-51/SMDI), available from Penederm Inc. It has been found that the combination of the film-forming agent with the long chain alcohol, esters and wax results in a long-wearing lipstick which is moisturizing, softening, and has shine.

Evaporative Solvents

Although not necessary to achieve long-wearing properties, the composition may also include evaporative silicone solvents to further improve the long-wear properties of the cosmetic. Evaporative solvents are solvents which have a vapor pressure of at least 0.01 mm of Hg at 20° C. and a viscosity of between 0.5 and 10 centipoise at 25° C. The evaporative solvents may be further classified as volatile solvents and near volatile solvents.

Volatile Solvents

The volatile solvents include low viscosity silicone fluids having a viscosity between 0.5 and 5.0 centipoise at 25° C., and a vapor pressure of at least 0.8 mm Hg and more preferably at least 2 mm Hg at 25° C., including cyclic silicones of the formula:

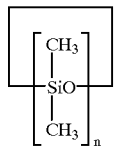

wherein n=3–7. Volatile linear polydimethyl siloxanes may also be used. These generally have about 2 to 9 silicon atoms and are of the formula:

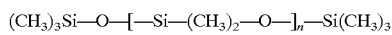

where n=0–7. Volatile silicone derivatives useful in the present invention include those known in the art. For example, one can use cyclomethicones such as DC 244, DC 245, DC 344, DC 345, 200 Fluid® 0.65 cs., and 200 Fluid® 1.0 cs., available from Dow Corning. It may be necessary to use mixtures of the fluids to achieve the minimum vapor pressure. For example, the vapor pressure of DC 245 is only about 0.1 mm Hg at 25° C., thus it would be necessary to blend DC 245 with a more volatile solvent, such as Dow Corning 200® Fluid, 0.65 cs. to achieve the necessary volatility. The use of these highly volatile silicone derivatives is not preferred since they tend to evaporate too quickly from the surface of the skin, resulting in drying of the skin. It is believed that the combination of the volatile solvent with the long chain fatty alcohol will result in the volatile solvent not evaporating as quickly as it otherwise would, thereby reducing its drying effect on the skin as the volatile solvent evaporates.

"Near Volatile" Solvent

It has been found that silicone solvents having a vapor pressure of between 0.01 and about 0.14 mm Hg, more preferably between 0.01 and 0.10 mm Hg, and most preferably between about 0.01 and 0.05 mm Hg, a viscosity of greater than 4 centipoise, but less than 10 centipoise, preferably between 6 and 8 centipoise and most preferably from about 6 to about 7 centipoise, provide surprisingly beneficial results of improving the wear of the lipstick without excessive drying of the skin. Suitable near volatile silicone solvents include DC 245, DC 246, DC 345, and Dow Corning 200® Fluid, 1.5 cs., Dow Corning 200® Fluid, 2.0 cs., Dow Corning 200® Fluid, 5.0 cs., and mixtures. The most preferred of these silicone solvents, for convenience termed "near volatile solvent," is the DC 246 sold by Dow Corning. DC 246 contains 92% of cyclohexane siloxane, often termed a "hexamer" or "$D_6$ cyclomethicone." The chemical name is dodecamethylcyclohexasiloxane. DC 246 fluid also contains a small percentage (2%) of the pentomer, i.e., $D_5$ and about 5% of the $D_7$ cyclomethicone. The DC 246 has a viscosity of about 6.5 to about 7.3 centipoise at 25° C. and a vapor pressure of about 0.002 mm Hg at 20° C.

It is believed that the combination of this near volatile solvent with the long chain fatty alcohol results in the near volatile solvent not evaporating as quickly as it otherwise would, thereby still further reducing the possibility of drying of the skin as the near volatile solvent evaporates.

A cross-linked polymer may be included in the composition. Suitable cross-linked polymers include porous microspheres which are capable of adsorbing components from the cosmetic composition. Microspheres are sold by Advanced Polymer System, Inc. under the trade name Microsponge®. Similar to the Microsponge® are cross-linked polymethacrylate copolymers sold generally under the name Polytrap®, which are available from Dow Corning. Particularly preferred is the highly cross-linked polymethacrylate copolymer available as Polytrap® 6603, from Advanced Polymers System, Inc. and as Polytrap Q5 6603 from Dow Corning. Polytrap® Q5 6603 (and Polytrap® 6603) has a unique morphology consisting of unit particles less than one micron in size which are associated into agglomerates of 20 to 80 microns in size. These agglomerates are electrostatically aggregated into macro-particles 20 to 1200 microns in size. Since these aggregates are weakly structured, the material breaks apart upon rubbing on the skin, conveying a lubricious skin feel and allowing the particles to disappear on the skin. The Polytrap® Q5 6603 is capable of containing as much as 4 times its weight of the liquid components in the cosmetic. The adsorption activity is a physical phenomenon controlled by the surface tension of the fluids on the polymer powder surface and the filling of interstitial voids by capillary action. Since the material is strongly oleophilic, but hydrophobic, it controls oils and lipids on the skin, without overdrying. The following table summarizes the Polytrap Q5 6603 properties:

| | |
|---|---|
| Color | White |
| Surface Energy, mNm$^{-1}$ | 39.6 |
| Particle Size, microns | 200–1200 |
| Fundamental Particle Size, microns | <1 |
| Apparent Density, g/cc | 0.06 |
| Surface Area, m$^2$/cm$^3$ | 0.32 |
| Void Volume, cc/g | 13.6 |

The composition of the invention may also include any additive conventionally used in the cosmetics or dermatological filed, such as, but not limited to antioxidant, fragrances, essential oils, preservatives, thickeners, cosmetic active principles, moisturizers, botanical extracts, vitamins, dyes, pigments, essential fatty acids, $C_8$–$C_{18}$ isoparaffin, volatile oils such as isodecane, isododecane, and isohexadecane, or sunscreens.

The composition may contain a particulate phase generally composed of fillers and pigments. This particulate matter may be present in the composition in an amount ranging form 0.1 to 25%, including 0.5 to 20% as well as 1 to 18% by weight of the total composition. The particulate matter has a particle size of 0.5 to 200 microns, including 1 to 100 microns, preferably below about 4 microns. The particulate matter may be colored or non-colored (e.g., white). Suitable powders include bismuth oxychloride, titanated mica, fumed silica, spherical silica, polymethylmethacrylate, micronized teflon, boron nitride, acrylate copolymers, aluminum silicate, aluminum starch, octenylsuccinate, bentonite, calcium silicate, cellulose, chalk, corn starch, diatomaceous earth, fuller's earth, glyceryl starch, hectorite, hydrated silica, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixture thereof. The above mentioned powders may be surface treated with lecithin, amino acids, mineral oil, silicone oil or various other agents either alone or in combination, which coat the powder surface and render the particles more lipophilic in nature.

The particulate matter component also may comprise various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof.

The composition may contain a mixture of both pigmented and non-pigmented powders. The percentage of pigments used in the powder component will depend on the type of cosmetic being formulated.

In one embodiment, the composition of the invention may be an anhydrous cosmetic composition in the form of a continuous fatty phase containing at least one wax, at least one ester, and at least one long chain alcohol. The composition may additionally contain at least one volatile silicone derivative. Further, the composition does not contain any fluorinated oils. Specifically, in a particularly preferred embodiment, the composition may comprise ozokerite, polyethylene, and microcrystalline wax; dipentaerythrityl tetrahydroxystearate/isostearate and triisostearyl citrate; octyldodecanol; and cyclomethicone. Preferably the composition also includes a film-forming agent such as polyvinyl pyrrolidone/hexadecene copolymer and a moisturizing agent such as LIPODERMOL LS 8656, available from Laboratoires Sérobiologiques.

In a still further preferred embodiment, the cosmetic will include silica. The silica in combination with the LIPODERMOL LS 8656 and the triisostearyl citrate and a dipentaerythrityl tetrahydroxystearate/isostearate improves the mass release of the mixture.

In a particularly preferred embodiment, one combines the LIPODERMOL LS 8656 with the triisostearyl citrate, the dipentaerythrityl tetrahydroxystearate/isostearate, silica, long-chain fatty alcohol, high melting point cosmetic waxes such as polyethylene, ozokerite and microcrystalline wax, polyglyceryl-2 triisostearate, and the Polytrap® 6603 result in a cosmetic having excellent adhesive properties, moisturizing effects, long-wear, shine and, when formulated into a lipstick, increased stick stability in high temperature and high humidity conditions without the need to change the texture of the product. In addition, the use of the polyglyceryl-2 triisostearate results in improved pigment dispersion in the lipstick. The combination of these properties results in a superior product.

The composition of the invention may be in the form of, for example, a make-up foundation, an eyeshadow, an eyeliner, a blush, a concealer, a mascara, a lipstick or a lip composition. The composition may be in the form of a stick, a cream or a soft paste. The composition may be in stick form, poured into a pan or other types of cake or cream forms.

The cosmetic composition of the invention can provide good adhesion to the skin, have good film-forming properties, be long-wearing, have shine, and additionally can provide moisturizing and softening. The invention will be further clarified by the following examples, which are intended to be illustrative of the invention but not limiting thereof.

EXAMPLE 1

A lipstick composition having the following composition was prepared:

| | |
|---|---|
| Polyethylene | 5.74% |
| Ozokerite | 6.79% |
| Microcrystalline Wax | 2.73% |
| Dipentaerythrityl tetrahydroxystearate/isostearate | 14.70% |
| Triisostearyl citrate | 18.90% |
| Octyldodecanol | 24.27% |
| LIQUAPAR OIL (preservative) available from ISP | 0.40% |
| BHT | 0.05% |
| GANEX V-216 | 1.50% |
| Purified Ester Gum | 0.70% |
| Phenyl Trimethicone | 1.40% |
| Quaternium-18 hectorite (BENTONE 38 from Rheox) | 0.56% |
| Propylene carbonate | 0.11% |
| Silica | 1.05% |
| Titanium Dioxide | 3.20% |
| Red Iron Oxide | 4.80% |
| FDC Yellow No. 5 Aluminum Lake | 0.50% |
| Black Iron Oxide | 0.30% |
| DC Red No. 7 Calcium Lake | 1.20% |
| Polyglyceryl-2 Triisostearate | 2.70% |
| Aloe Vera Extract | 1.00% |
| LIPODERMOL LS 8656 | 1.00% |

-continued

| | |
|---|---|
| Acrylates copolymer (Polytrap ® Q5 6603) | 0.80% |
| Cyclomethicone (DC 246) | 5.60% |

EXAMPLE 2

| | |
|---|---|
| Octyldodecanol | 22.854 |
| Triisostearyl citrate | 18.904 |
| Lanolin | 14.698 |
| Mica (and) Titanium Dioxide (and) Carmine | 8.778 |
| Ozokerite | 6.791 |
| Polyethylene | 5.738 |
| Cyclomethicone (DC 246) | 5.600 |
| Microcrystalline Wax | 2.735 |
| Polyglyceryl-2 Triisostearate | 2.696 |
| Mica (and) Titanium Dioxide (and) Iron Oxide | 2.310 |
| PVP/Hexadecene Copolymer | 1.477 |
| Phenyl Trimethicone | 1.394 |
| Silica | 1.053 |
| Aloe Vera Extract | 1.000 |
| Octyldodecanol, Lecithin, Arachidyl Propionate, Tocopherol Acetate, Retinyl Palmitate, Linoleic Acid (and) Linolenic Acid | 1.000 |
| Acrylates Copolymer (Polytrap ® Q5 6603) | .795 |
| Glycerol Rosinate (and) Octyldodecyl Myristate | .702 |
| Quaternium-18 Hectorite | .560 |
| Isopropyl Paraben (and) Isobutylparaben (and) N-Butylparaben | .415 |
| D & C Red No. 7 - Calcium Lake | .176 |
| F D & C Yellow No. 6 - Aluminum Lake | .120 |
| Titanium Dioxide | .102 |
| Propylene Carbonate | .056 |
| BHT | .046 |

The lipstick composition adhered well to the lips, provided a comfortable film which did not feel dry or tight, and exhibited notable long-wearing properties. These compositions can be prepared according to generally known methods in the art, such as is described in U.S. Pat. No. 5,690,918.

It will be apparent to those skilled in the art that various modifications and variations can be made in the compositions of the invention without departing from the spirit or scope of the invention. Thus, it is intended that the present invention cover the modifications and variations of this invention provided that they come within the scope of the appended claims and their equivalents.

What is claimed is:

1. A long-wearing cosmetic composition comprising:
   a) an evaporative solvent having a viscosity of 0.5 to 10 centipoise at 25° C., and a vapor pressure of at least 0.01 mm Hg at 20° C.,
   b) from about 5% to about 40% of an ester of an acid having at least 4 carbon atoms,
   c) from 1% to 40% of a long-chain alcohol containing from 12 to 48 carbon atoms,
   d) from about 1% to about 35% of a wax, and
   e) a particulate phase.

2. The cosmetic composition of claim 1 wherein said acid is citric acid.

3. The cosmetic composition of claim 1 wherein said ester is triisostearyl citrate.

4. The cosmetic composition of claim 1 herein said evaporative solvent is a volatile silicone.

5. The cosmetic composition of claim 4 wherein said volatile silicone is a cyclomethicone.

6. The cosmetic composition of claim 5 wherein said wax is a polyethylene wax.

7. The cosmetic composition of claim 6, comprising:
   a) a volatile silicone having a viscosity of 0.5 to 5 centipoise at 25° C., and a vapor pressure of at least 2 mm Hg at 20° C.,
   b) from about 5% to about 40% of triisostearyl citrate, and
   c) from about 1% to about 35% of a polyethylene wax.

8. A long-wearing cosmetic composition comprising:
   a) from about 5% to about 40% of an ester of an acid having at least 4 carbon atoms,
   b) from 1% to 40% of a long-chain alcohol containing from 12 to 48 carbon atoms,
   c) from about 1% to about 35% of a wax, and
   d) a particulate phase.

9. The cosmetic composition of claim 8 wherein said acid is citric acid.

10. The cosmetic composition of claim 9 wherein said ester is triisostearyl citrate.

11. The cosmetic composition of claim 16 wherein a volatile solvent is present.

12. The cosmetic composition of claim 11 wherein said volatile silicone is a cyclomethicone.

13. The cosmetic composition of claim 12 wherein said wax is a polyethylene wax.

14. The cosmetic composition of claim 8, comprising:
   a) a volatile silicone,
   b) from about 5% to about 40% of triisostearyl citrate, and
   c) from about 1% to about 35% of a polyethylene wax.

15. A pigmented cosmetic stick composition comprising, by weight of the total composition:
   a) 1–40% of a volatile nonaqueous solvent having a viscosity of 0.5 to 5 centipoise at 25° C., and a vapor pressure of at least 2.0 mm Hg at 20° C.,
   b) 20–80% of a first nonvolatile oil which is a $C_{12-22}$ fatty ester of citric acid,
   c) 1–35% of a second nonvolatile oil,
   d) 1–30% of a wax having a melting point of 30 to 135° C. which is an ethylene homopolymer or ethylene copolymer,
   e) 0.1–25% of particulate matter having a particle size of 0.5 to 200 microns; and
   wherein the total amount of nonvolatile oil present in the stick is greater than about 31% by weight of the total composition.

16. The composition of claim 15, wherein the volatile nonaqueous solvent is a volatile silicone.

17. The composition of claim 16, wherein the volatile silicone is selected from the group consisting of:
   a) a cyclic silicone having the formula:

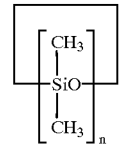

wherein n=3.7
   b) a volatile linear polydimethylsiloxane having the formula:

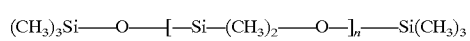

wherein n=0.7 c) straight or branched chain paraffinic hydrocarbons having 5–20 carbon atoms; and d) mixtures thereof.

18. The composition of claim 16 wherein the volatile solvent is a cyclic silicone.

19. The composition of claim 15 wherein the fatty ester of citric acid is the reaction product of a $C_{16-22}$ fatty alcohol with citric acid.

20. The composition of claim 15 wherein the fatty alcohol is stearyl alcohol.

21. The composition of claim 15 wherein the fatty ester of citric acid is triisostearyl citrate.

22. The composition of claim 15 wherein the second nonvolatile oil has a viscosity of about 10 to 1,000,000 centipoise at 25° C.

23. The composition of claim 22 wherein the second nonvolatile oil is selected from the group consisting of:

a) esters of the formula $RCO\text{---}OR^1$ wherein R and $R^1$ are each independently a $C_{1-25}$, preferably a $C_{4-20}$, straight or branched chain alkyl, alkenyl or alkoxycarbonylalkyl or alkylcarbonyloxyalkyl, b) glyceryl esters of fatty acids, c) nonvolatile hydrocarbons, d) straight or branched chain fatty alcohols of the formula R—OH, wherein R is a straight or branched chain saturated or unsaturated alkyl having 8–48 carbon atoms, e) nonvolatile silicones, f) guerbet esters; and g) mixtures thereof.

24. The composition of claim 16 wherein the nonvolatile oil is selected from the group consisting of dimethicone, nonvolatile hydrocarbons, and esters of the formula $RCO\text{---}OR^1$ wherein R and $R^1$ are each independently a $C_{1-25}$, preferably a $C_{4-20}$ straight or branched chain alkyl, alkenyl or alkoxycarbonylalkyl or alkylcarbonyloxyalkyl.

25. The composition of claim 8 wherein the nonvolatile oil is dimethicone.

26. The composition of claim 8 wherein the wax contains ethylene monomer units in either repetitive or random sequence.

27. The composition of claim 19 wherein comprises wax ethylene monomer units in either repetitive or random sequence, in combination with monomer units of the following formula:

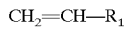

wherein $R_1$ is a $C_{1-30}$ straight or branched chain saturated or unsaturated alkyl, aryl, or aralkyl, preferably a $C_{1-20}$ straight or branched chain alkyl.

28. The composition of claim 8 wherein the particulate matter comprises a mixture of pigments and powders.

29. The composition of claim 21 wherein the pigments are organic pigments.

30. The composition of claim 8, additionally comprising 0.0001–3% by weight of the total composition of ceramides.

31. The composition of claim 8 additionally comprising 0.001–5% by weight of the total composition of plant extracts.

32. The composition of claim 8 additionally comprising 0.001–4% by weight of the total composition of carbohydrates.

33. The composition of claim 8 additionally comprising 0.001–5% by weight of the total composition of sterols.

34. The composition of claim 8 additionally containing 0.001–5% by weight of the total composition of humectants.

35. A long-wearing cosmetic composition comprising:

a) from about 5% to about 40% of an ester of an acid having at least 4 carbon atoms, b) from 1% to 40% of a long-chain alcohol containing from 12 to 48 carbon atoms, c) from about 1% to about 35% of a wax, and d) a particulate phase.

36. The long-wearing cosmetic composition of claim 28 wherein said ester is triisostearyl citrate.

37. A long-wearing cosmetic composition comprising:

a) a near volatile solvent having a viscosity of from 4 to 10 centipoise at 25° C., and a vapor pressure of 0.01 to 0.14 mm Hg at 20° C.

b) from about 5% to about 19% of an ester of an acid having at least 4 carbon atoms, c) from 1% to 40% of a long-chain alcohol containing from 12 to 48 carbon atoms, d) from about 1% to about 35% of a wax, and e) a particulate phase.

38. The long-wearing cosmetic composition of claim 30 wherein said ester is triisostearyl citrate.

39. The long-wearing cosmetic composition of claim 37 wherein the near-volatile solvent comprises about 92 percent of cyclohexasiloxane.

40. The long-wearing cosmetic composition of claim 39 wherein a highly cross-linked polymethacrylate copolymer comprising unit particles less than one micron which are associated into agglomerates of 20–80 microns.

41. The long-wearing cosmetic composition of claim 40 wherein said long-chain alcohol is octyldodecanol and said ester of an acid having at least 4 carbon atoms is triisostearyl citrate.

42. The long-wearing cosmetic composition of claim 41, wherein said compositions further comprises dipentaerythrityl tetrahydroxystearate/isostearate.

* * * * *

UNITED STATES PATENT AND TRADEMARK OFFICE
CERTIFICATE OF CORRECTION

PATENT NO. : 6,444,212 B1
DATED : September 3, 2002
INVENTOR(S) : Roberto Cavazzuti et al.

It is certified that error appears in the above-identified patent and that said Letters Patent is hereby corrected as shown below:

Column 8,
Line 20, "16" should read -- 10 --.

Signed and Sealed this

Seventh Day of January, 2003

JAMES E. ROGAN
*Director of the United States Patent and Trademark Office*